US012148511B2

(12) United States Patent
Yundt-Pacheco et al.

(10) Patent No.: US 12,148,511 B2
(45) Date of Patent: Nov. 19, 2024

(54) SYSTEM AND METHOD FOR CONDUCTING VIRTUAL CROSSOVER STUDIES IN CLINICAL DIAGNOSTIC PROCESSES

(71) Applicant: Bio-Rad Laboratories, Inc., Hercules, CA (US)

(72) Inventors: John Yundt-Pacheco, Fairview, TX (US); Curtis Parvin, Garland, TX (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 818 days.

(21) Appl. No.: 17/338,937

(22) Filed: Jun. 4, 2021

(65) Prior Publication Data
US 2022/0199206 A1    Jun. 23, 2022

Related U.S. Application Data (63) Continuation of application No. PCT/US2020/066563, filed on Dec. 22, 2020.

(51) Int. Cl.
*G16H 10/40* (2018.01)
(52) U.S. Cl.
CPC .................. *G16H 10/40* (2018.01)
(58) Field of Classification Search
CPC .................................................. G16H 10/40
See application file for complete search history.

(56) References Cited

U.S. PATENT DOCUMENTS

| | | | | |
|---|---|---|---|---|
| 8,645,306 | B2 * | 2/2014 | Hammond | G01N 35/00693 706/52 |
| 10,658,076 | B2 * | 5/2020 | Gulati | G16H 10/60 |
| 2005/0037502 | A1 * | 2/2005 | Miller | G01N 35/00 436/43 |
| 2007/0192134 | A1 * | 8/2007 | Littenberg | G16H 70/20 600/300 |

(Continued)

FOREIGN PATENT DOCUMENTS

| | | | | |
|---|---|---|---|---|
| JP | 6971534 | B2 * | 11/2021 | H01M 4/8626 |
| RU | 2572226 | C1 * | 12/2015 | |

OTHER PUBLICATIONS

Aris-Brosou S, Kim J, Li L, Liu H. Predicting the Reasons of Customer Complaints: A First Step Toward Anticipating Quality Issues of In Vitro Diagnostics Assays with Machine Learning. JMIR Med Inform. May 15, 2018;6(2):e34. doi: 10.2196/medinform. 9960. PMID: 29764796; PMCID: PMC5974458. (Year: 2018).*

(Continued)

*Primary Examiner* — Sun M Li
(74) *Attorney, Agent, or Firm* — AVEK IP, LLC; Mark C. Young (57) ABSTRACT

A clinical diagnostic analyzer for performing a virtual crossover study on quality control (QC) material includes a processor, memory, measurement hardware, and an input panel/display. The analyzer acquires data from a peer group relating to a new lot of quality control material to calculate a predicted mean and standard deviation based on that peer group data and adjusted for bias in the laboratory process. As (Continued)

new analyses are run on the new lot of QC material, the predicted mean and standard deviation are updated to incorporate the actual data on a weighted basis.

15 Claims, 5 Drawing Sheets

(56) References Cited

U.S. PATENT DOCUMENTS

| | | | | |
|---|---|---|---|---|
| 2012/0035442 A1* | 2/2012 | Barman | G01J 3/0208 | |
| | | | 600/316 | |
| 2012/0330866 A1* | 12/2012 | Parvin | G06F 11/24 | |
| | | | 706/12 | |
| 2016/0012191 A1* | 1/2016 | Kuchipudi | G16H 50/20 | |
| | | | 702/19 | |
| 2016/0132375 A1* | 5/2016 | Jacobs | G16H 40/40 | |
| | | | 714/47.2 | |
| 2019/0035490 A1* | 1/2019 | Cembrowski | G16H 50/20 | |

OTHER PUBLICATIONS

Chen X, Wang J, Zhang W, Xie E, Zhang B, Xu HG. Failure of internal quality control in detecting significant reagent lot shift in serum creatinine measurement. J Clin Lab Anal. Nov. 2019;33(9):e22991. doi: 10.1002/jcla.22991. Epub Aug. 2, 2019. PMID: 31373724; PMCID: PMC6868421. (Year: 2019).*

Blanchard IE, Kozicky R, Dalgarno D, Simms J, Goulder S, Williamson TS, Biesbroek S, Page L, Leaman K, Snozyk S, Redman L, Spackman K, Doig CJ, Lang ES, Lazarenko G. Community paramedic point of care testing: validity and usability of two commercially available devices. BMC Emerg Med. May 2, 2019;19(1) (Year: 2019).*

Merves et al., "Quality Assurance, Quality Control and Method Validation in Chromatographic Applications", Chromatographic Methods in Clinical Chemistry and Toxicology, Feb. 2007, pp. 1-14, John Wiley & Sons, Ltd., University of Florida, College of Medicine, Gainesville, Florida, USA.

* cited by examiner

SYSTEM AND METHOD FOR CONDUCTING VIRTUAL CROSSOVER STUDIES IN CLINICAL DIAGNOSTIC PROCESSES

CROSS-REFERENCE TO RELATED APPLICATIONS

This application is a continuation of, and claims the benefit of, International Application Number PCT/US2020/066563, filed Dec. 22, 2020, the disclosure of which is hereby incorporated herein in its entirety by reference.

BACKGROUND OF THE INVENTION

The present invention relates to generally to clinical diagnostic processes, and more particularly to systems and methods for conducting virtual cross over studies in such processes using clinical diagnostic analyzers and systems and peer groups comprising such analyzers.

Clinical diagnostic laboratories use various quality control schemes to ensure that the clinical diagnostic processes employed and the clinical diagnostic analyzers used to analyze patient specimens, or other test specimens, provide accurate diagnostic results. One common quality control scheme involves testing quality control (QC) materials having known properties using the same analyzers and processes that are used to test patient specimens. Running such quality control tests with material having known properties ensures that the clinical diagnostic analyzers used to perform the test provide expected and accurate results, or provide results within a predetermined range or specification, and likewise ensures that the reagents and processes used in conjunction with the analyzers provide expected results.

While quality control testing using quality control material having known properties is generally useful, statistical control issues arise when the quality control materials must be replenished. Because the quality control materials have a limited lifetime, and because QC testing using the quality control material consumes that material, laboratories must regularly deal with obtaining and using new lots of quality control materials, requiring them to crossover and begin using the new lot of QC material. Crossing over to the new QC material is a substantial undertaking for a laboratory, as the reliability and accuracy of the new quality control material must be ensured before proceeding with further testing relying on the new quality control materials. Even though the new lot of QC control material will have similar properties to the previous lot, the variations between lots will affect the accuracy of the testing, particularly until a sufficient number of tests can be run on the new QC materials. And, even if another laboratory has already switched over to a new lot of quality control material, the data from that other laboratory cannot simply be used by a separate laboratory as the biases implicit in each laboratory's test methods and equipment would result in inaccuracies if using data from another laboratory.

Thus, laboratories must engage in crossover studies to verify the accuracy of the new materials before the desired accuracy of the testing can be ensured. Such crossover studies must be done for any change in quality control materials, because even with quality control materials that have insert ranges, i.e., assayed quality control materials, insert ranges are only intended for laboratories to quickly determine if they are in control, they are not intended for use for performance monitoring.

Crossover studies typically involve determining the statistical behavior of a new lot of QC control material, namely, calculating or estimating the mean and standard deviation (SD) of the new material. In order to obtain that mean and SD measurement, the general approach for crossover studies is to evaluate samples and collect data of the new quality control material over time until sufficient data has been collected to compute the mean and SD from the collected data, then, once calculated, using and assigning that computed mean and SD for future control testing using the new quality control materials.

One generally accepted method of making that initial assessment is that described in *Statistical Quality Control for Quantitative Measurement Procedures: Principles and Definitions; Approved Guideline—Third Edition*, which calls for making a minimum of at least twenty different measurements of quality control material, for each control level, on separate days. That generally accepted method thus requires collecting at least twenty data points per control level, over a period of twenty days. Thus, for example, for a trilevel control involving thirty separate analytes, ninety separate studies must be conducted with a data point collected for each individual test. That collected data is then used to estimate a mean and SD for the new lot of material. In addition to the time required, such studies incur expense for the laboratory, with each molecular data point collected during testing incurring separate costs. Such studies are also labor intensive. As there is no standardized system for conducting such crossover studies, most laboratories typically manually process the collected data using a spreadsheet, and manually input the data to calculate the mean and SD of the new quality control material.

Even after incurring the time, expense, and inefficiency of conducting crossover studies in accordance with the generally recommended procedures, the results of those studies do not have the accuracy desired or required by the laboratory. For example, while twenty data points is sufficient to determine the mean of the new material, collecting that number of data points is not necessary and is thus inefficient, as the mean can be determined by using just ten data points. Thus, the generally recommended crossover study method incurs unnecessary testing and expense with respect to determining the mean. Furthermore, twenty data points is insufficient to determine the SD with a desired level of accuracy, typically eighty data points are required. Using the generally recommended method thus typically results in estimated SD's having a high error margin.

Recognizing the above limitations, the industry has suggested an alternative for determining the SD of the new control material based on using only ten data points by incorporating the mean and SD of the old material, using the equation $SD_{new} = (MEAN_{new} * CV_{old}/100$, where $CV_{old} = 100 * (SD_{old}/MEAN_{old})$. However, while that that alternative determination requires a fewer number of data points, and thus takes less time, the results using that method still incur potential inaccuracies in the mean calculation (see, e.g., C24 *Statistical Quality Control for Quantitative Measurement Procedures: Principles and Definitions, 4th Edition*).

Regardless of the calculation used, known methods of conducting crossover studies require that each individual laboratory run analyses on the new lot of quality control material and complete the crossover study before testing of patient specimens, for example, can begin.

Thus, it is apparent that there remains a need in the art for systems and methods for conducting crossover studies that expedite the process and overcome deficiencies of methods known in the art.

BRIEF SUMMARY OF THE INVENTION

The present invention is directed to a system and method for conducting virtual crossover studies in clinical diagnostic processes using clinical diagnostic analyzers and in systems, groups of systems, and peer groups of systems employing clinical diagnostic analyzers.

In an exemplary embodiment, the system and method of the present invention employ one or more clinical diagnostic analyzers to conduct a virtual crossover study for a new lot of quality control material by relying on data associated with the new lot of material gathered from a peer group of similar laboratories that are already using the new lot of quality control material and have already gathered data from that new lot of material. Using comparative data to relate data from a prior, or old, lot of quality control material to account for bias in the separate laboratories, a predicted mean and standard deviation for the new lot of quality control material is calculated prior to evaluating or analyzing any of the new lot of material. Using a Bayesian approach, an estimate for the lab mean of the new lot of control material is generated using peer statistics from the new lot of control material prior to the evaluation by the lab of the new lot of control material. Lab data for the new lot of control is incorporated in a weighted fashion to update the estimate of the lab mean for the new lot of control material, which is further used to estimate the SD of the new lot of control material.

In one aspect, a virtual crossover study can be instigated on a new lot of quality control material by using data from a peer group with respect to prior lot numbers of quality control material and with respect to the new lot number as collected by the peer group. Calculating estimated or predicted mean and standard deviation (SD) values from the peer group data, the crossover study at a laboratory can begin before any new analyses are performed on the new lot of quality control material. As testing continues and new analyses are performed on the new lot of quality control material, the actual data is integrated into the calculation of the predicted values up until at least a desired target number of new data points have been collected—typically at least ten—at which time the calculations of mean and SD continue, using only actual collected data. In a further aspect, the data from the completed analyses is weighted in the calculations to give more preference to the actual data as it is collected.

In another aspect, a clinical diagnostic analyzer for performing a virtual crossover study includes a processor, memory, measurement hardware, and an input panel/display. The analyzer prompts a user to begin a virtual crossover study and accesses data from a peer group with respect to new and old lots of QC material. The analyzer calculates an estimated mean and standard deviation for the new lot of QC material, and further prompts a user to load, or automatically loads, a QC specimen from the new lot of material and instigates testing and analysis to determine a mean and a standard deviation for the new material.

In another aspect, a group of laboratories, each comprising one or more clinical diagnostic analyzers, are in communication with each other in a peer group configuration, where information and data is shared between the members of the peer group. Shared information may comprise data regarding analyses performed and information relating to quality control material used in the laboratory.

In another aspect, the peer group estimated mean and SD values allow a laboratory to proceed as if a crossover study is complete—using the predicted mean and SD values—while analyses on the new lot of quality control material are still underway. Thus, the impact of the crossover study to the operation of the laboratory is minimized.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings and claims. In the drawings, like reference numbers indicate identical or functionally similar elements.

BRIEF DESCRIPTION OF THE DRAWINGS

The present invention will be described in greater detail in the following detailed description of the invention with reference to the accompanying drawings that form a part hereof, in which.

DETAILED DESCRIPTION OF EXEMPLARY EMBODIMENTS

Systems and methods for conducting virtual crossover studies of quality control materials in laboratories using a clinical diagnostic analyzer, in groups of clinical diagnostic analyzers, in systems comprising clinical diagnostic analyzers, and in systems of clinical diagnostic analyzers connected in peer groups in accordance with exemplary embodiments of the present invention are described herein. While the invention will be described in detail hereinbelow with reference to the depicted exemplary embodiments and alternative embodiments, it should be understood that the invention is not limited to the specific configurations shown and described in these embodiments. Rather, one skilled in the art will appreciate that a variety of configurations may be implemented in accordance with the present invention.

Figure 1:
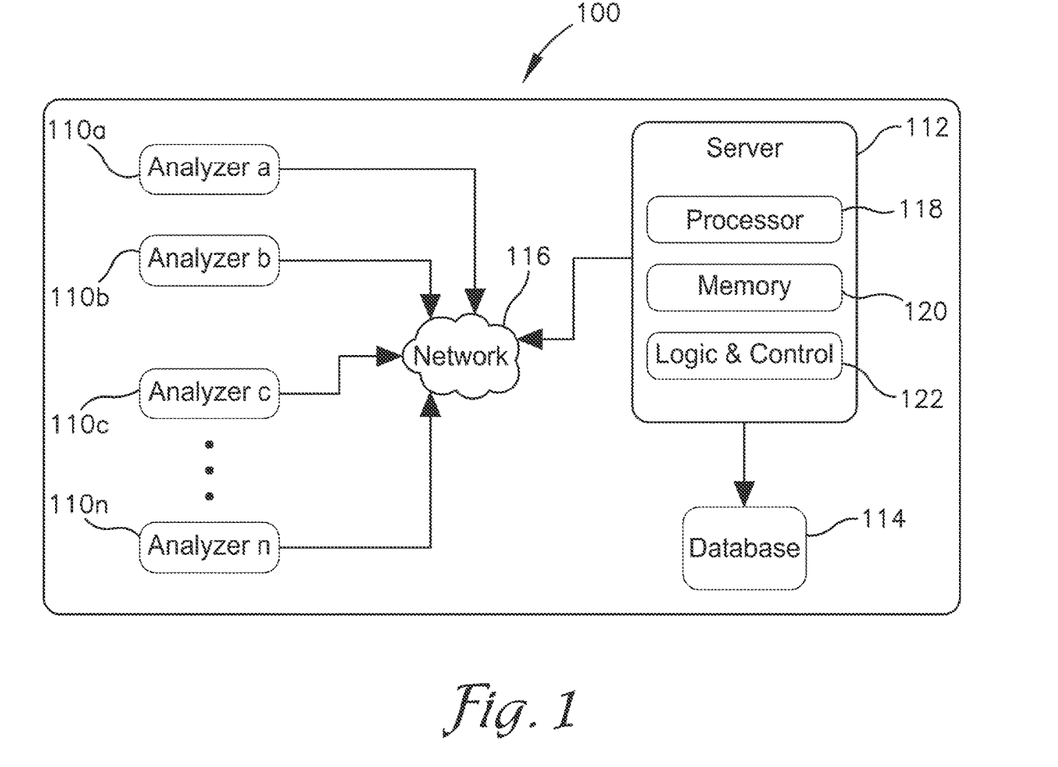
FIG. 1 depicts a block diagram of a clinical diagnostic analyzer system having a plurality of clinical diagnostic analyzers in communication with a server over a network in accordance with an exemplary embodiment of the present invention.

Looking first to FIG. 1, a clinical diagnostic system in accordance with an exemplary embodiment of the present invention is depicted generally by the numeral 100. The system 100 generally includes a plurality of clinical diagnostic analyzers 110a, 110b, 110c, 110n and a server 112 in communication with a database 114. The plurality of clinical diagnostic analyzers 110a, 110b, 110c, 110n are in communication with network 116, which facilitates the transmission of instructions, information, and data between each clinical diagnostic analyzer 110a, 110b, 110c, 110n and the server 112, as well as between each of the clinical diagnostic analyzers 110a, 110b, 110c, 110n and any of the other diagnostic analyzers, or between any combination of clinical diagnostic analyzers and/or the server.

Network 116 may be any local area network (LAN), wide area network (WAN), ad-hoc network, or other network configuration known in the art, or combinations thereof. For example, in the exemplary embodiment depicted in FIG. 1, network 116 may include a LAN allowing communication between the clinical diagnostic analyzers 110a, 110b, 110c, 110n, such as in a single laboratory setting having multiple clinical diagnostic analyzers, an may also include a WAN, such as the Internet or other wide area network, allowing communication between the LAN and the server 112 and/or between the clinical diagnostic analyzers and the server.

It should be understood that the configurations depicted in FIG. 1 is exemplary, and not limiting, and that the invention as described herein may be embodied in a single clinical diagnostic analyzer, in a group of clinical diagnostic analyzers co-located in a single laboratory or facility, and in group of clinical diagnostic analyzers that are geographically dispersed.

For example, multiple systems 100, each comprising one or more clinical diagnostic analyzers and servers may be located in a single laboratory, or in multiple laboratories dispersed across a facility or across the globe, all in communication via a WAN. It should be further understood that the present invention may be embodied in a single clinical diagnostic analyzer, or in a group of clinical diagnostic analyzers in communication with each other over a LAN or WAN, without a server or servers. These and other variations and embodiments will be apparent to those skilled in the art.

Figure 4:
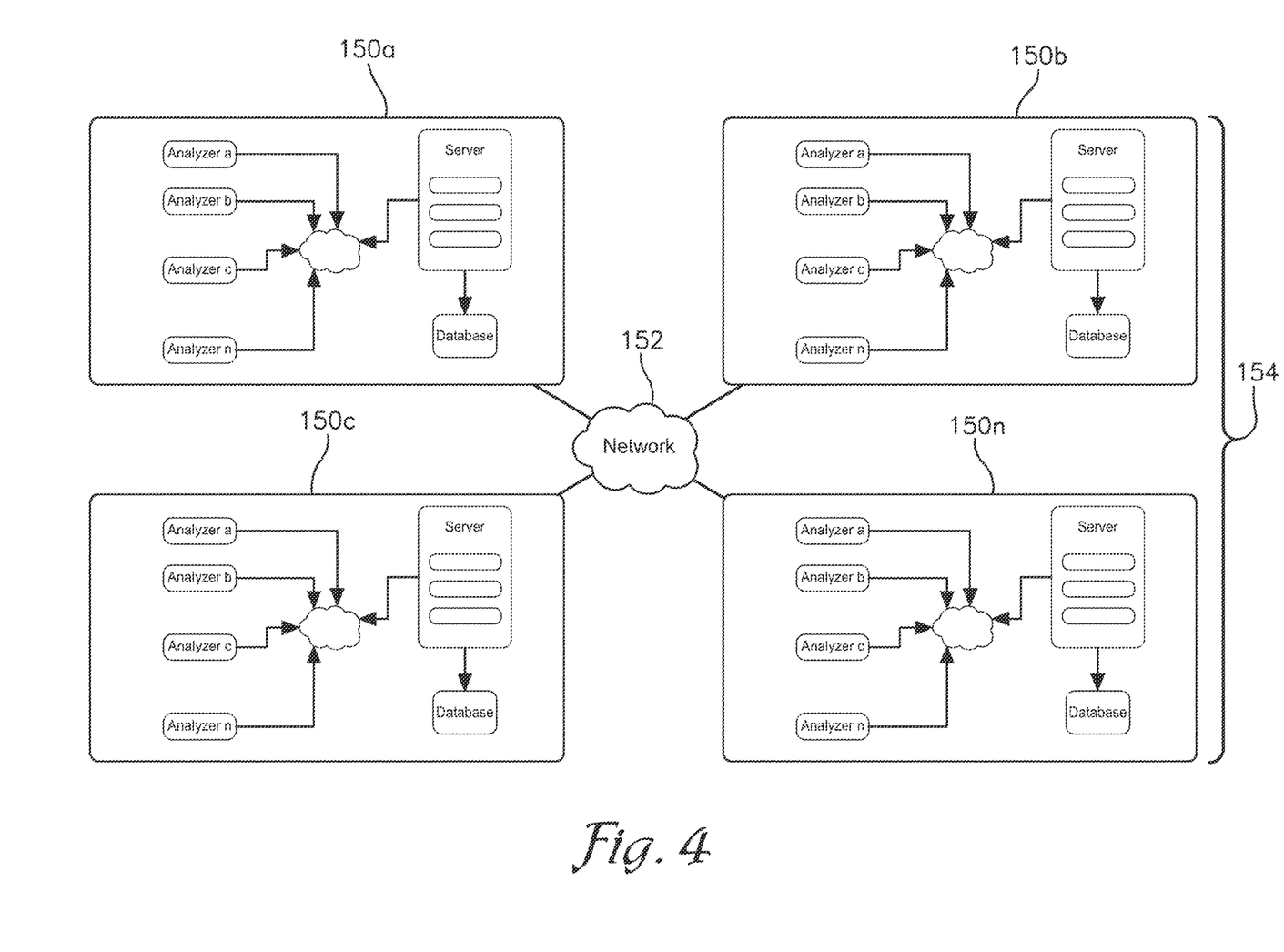
FIG. 4 is a block diagram of a plurality of clinical diagnostic analyzers as in FIG. 1 arranged in a peer group configuration.

In one exemplary embodiment, as depicted in FIG. 4, a plurality of clinical diagnostics systems 150a, 150b, 150c, 150n, such as those depicted in FIG. 1, are in communication via a network, such as the Internet or other WAN. This collection of separate systems comprises a peer group of systems 152, wherein each system 150a, 150b, 150c, 150n represents a laboratory having one or more clinical diagnostic analyzers, and wherein each of the laboratories conducts testing of patient specimens and quality control materials. Most preferably, each member 150a, 150b, 150c, 150n of the peer group 152 is a laboratory at a location geographically dispersed from the other peer group member laboratories, with each laboratory having similar types of clinical diagnostic analyzers, running similar types of tests and using quality control materials similar to those used by other peer members of the peer group.

Looking back to FIG. 1, server 112 preferably includes a processor 118, memory 120, and logic and control circuitry 122, all in communication with each other. Server 112 may be any server, server system, computer, or computer system known in the art, preferably configured to communicate instructions and data between the server 112 and the network, and/or to any device connected to the network, and to store and retrieve data and information to and from the database 114. Processor 118 may be any microprocessor, controller, or plurality of such devices known in the art. Processor 118 preferably runs a server operating system such as a Linux based, Windows based, or other server operating system known in the art. Preferably, the processor 118 is configured to control the operation of the server 112 in conjunction with the operating system, allowing the server to communicate with the database 114 and the network 116 and/or with devices connected to the network, such as the clinical diagnostic analyzers 110a, 110b, 110c, 110n. In some embodiments the server may control the operation of the clinical diagnostic analyzers, for example allowing operation of the analyzers during specific time periods, collecting data from the analyzers for storage in the database 114, transferring data to the analyzers for viewing and/or analysis, collecting test data from the analyzers, and providing data, instructions or prompts to the analyzers either individually or in groups.

Memory 120 may be volatile or non-volatile memory and is used to store data and information associated with the operation of the server as well as data for transmission to and from the server. For example, the memory stores the server operating system for execution by the processor 118 and may also store data associated with the clinical diagnostic analyzers 110a, 110b, 110c, 110n in communication with the server 112 over the network 116. In some embodiments the memory 120 on the server may be used as a supplement to, or in place of, the database 114.

The database 114 is preferably used to store control information relating to the operation of the server 112 and the operation and control of the clinical diagnostic analyzers 110a, 110b, 110c, 110n, and may also be used to store data relating to the processing of samples by the clinical diagnostic analyzers. For example, the database may contain instructions or programming for execution by a processor on a clinical diagnostic analyzer, or for execution on the server, or may store data related to the number of samples processed, the frequency of testing, the results of analysis performed on the analyzer, as well as data relating to the samples themselves, such as tracking information, lot numbers, sample size, sample weight, percentage of sample remaining, and the like. Preferably, the database 114 includes non-volatile storage such as hard drives, solid state memory, and combinations thereof.

Logic and control circuitry 122 provides interface circuitry to allow the processor and memory to communicate, and to provide other operational functionality to the server, such as facilitating data communications to and from the network 116.

Figure 2:
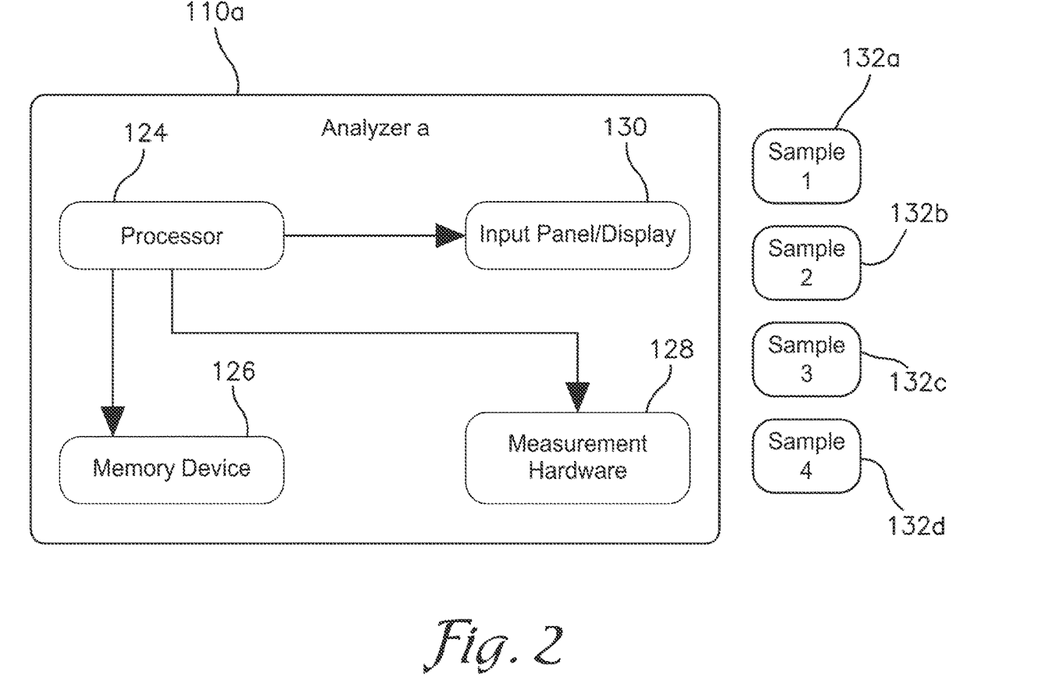
FIG. 2 depicts a block diagram of a single clinical diagnostic analyzer of the system of FIG. 1.

Turning to FIG. 2, a detailed view of a single clinical diagnostic analyzer 110a of the system of FIG. 1 is depicted. Clinical diagnostic analyzer 110a preferably comprises a processor 124, a memory device 126, measurement hardware 128, and an input panel/display 130.

The processor 124 may be any controller, microcontroller, or microprocessor as known in the art, and is in communication with memory device 126 which stores instructions for execution by the processor to control and communicate with the measurement hardware 128 and the input panel/display 130 to cause the clinical diagnostic analyzer to perform desired steps, such as sampling as commanding the measurement hardware to load test specimens or to perform a test on a loaded sample, or instructing or prompting an user to perform specific operations such as replacing a test sample, beginning a test, or viewing collected data. The processor 124 may also execute instructions to receive data from the measurement hardware 128 and to perform one or more analyses on the received data, and to display test results or other information on the input panel/display panel 130.

Measurement hardware 128 preferably includes a sample receptacle configured to receive one or more samples or specimens into the analyzer for testing. Preferably, the measurement hardware is configured to receive samples stored within vials, and most preferably is configured to receive a plurality of vials and to extract analytes, from any desired vial for and analysis. In further embodiments, the measurement hardware 128 may include external turntables, loaders, or other mechanisms to facilitate the loading and unloading of samples to allow samples to be loaded under command of the analyzer.

As depicted in FIG. 2, the measurement hardware is configured to be used with material samples 132a, 132b, 132c, 132d, which may be QC materials, patient test specimens or other specimens as is known in the art. In one embodiment, the material samples are contained in vials which are loaded or inserted into the clinical diagnostic analyzer 110a by a user. The samples may be loaded individually, or in groups, e.g., in a tray that is loaded into the analyzer. In alternative embodiments, the samples may be loaded using an automated loading mechanism, such as a turntable or other mechanism, upon command from the analyzer 110a. Material samples in the form of QC materials are typically provided in lots, with a unique lot number assigned to a lot of samples that are essentially identical as coming from the exact same batch source of material. The analyzer 110a preferably allows information relating to the QC materials to be entered by an user, including statistical information such as a mean or standard deviation for the lot of material. In other embodiments, the information may be obtained over a network or from a server using, for example a QR code on the sample vial or container to uniquely identify the sample or lot.

Input panel/display 130 is in communication with the processor and is operable to present controls to facilitate operation of the analyzer, as well as to present prompts and instructions to an user, and to receive input commands and/or data from the user. The input panel/display 130 is preferably a touch screen having capabilities of displaying text and graphics as well as icons, push buttons, keyboards, and the like to both present data to a user and to receive input from a user of the analyzer. Preferably, the input panel/display 130 includes an audible alert device such as a buzzer or beeper.

Figure 3A:
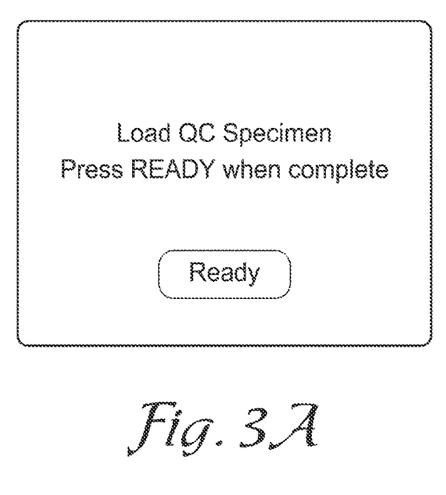
FIG. 3A is a depiction of a first exemplary prompt screen presented by the clinical diagnostic analyzer of FIG. 2.
Figure 3B:
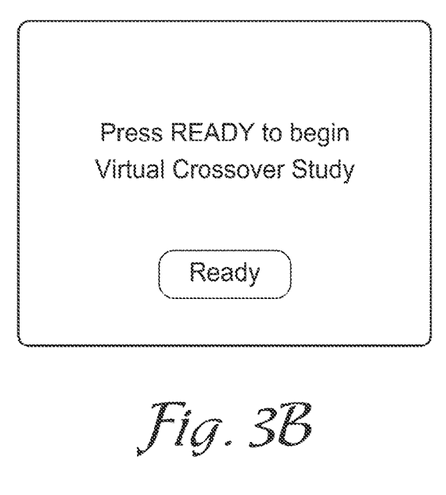
FIG. 3B is a depiction of a second exemplary prompt screen presented by the clinical diagnostic analyzer of FIG. 2.
Figure 3C:
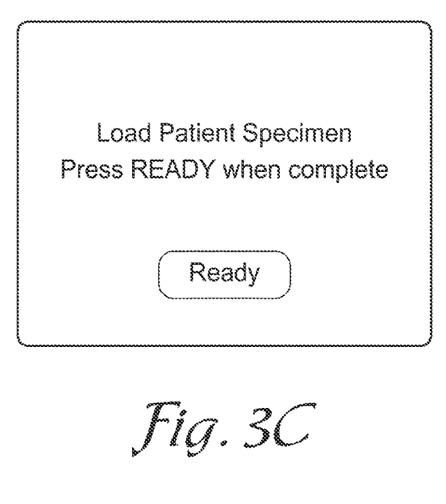
FIG. 3C is a depiction of a third exemplary prompt screen presented by the clinical diagnostic analyzer of FIG. 2.
Figure 3D:
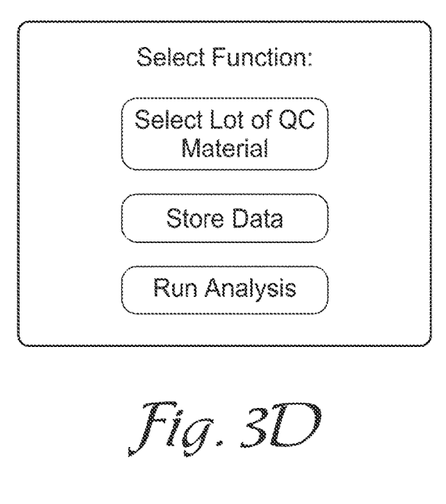
FIG. 3D is a depiction of a fourth exemplary prompt screen presented by the clinical diagnostic analyzer of FIG. 2.

Looking to FIGS. 3A, 3B, 3C, and 3D, for example, the input panel/display may present prompts to a user to load one a QC specimens and press a READY button once completed (FIG. 3A), to begin a virtual crossover study (FIG. 3B), to load a patient specimen (FIG. 3C) or to select a lot of material to use for a study, store data, or run an analysis (FIG. 3D). It should be understood that the clinical diagnostic analyzer 100a may have multiple programs and functions available, a menu or selection prompt is preferably presented to guide a user through the operation of the analyzer and the selection of desired functions and operations.

Clinical diagnostic analyzer 110a may be any type of analyzer known in the art, such as biochemistry analyzers, hematology analyzers, immune-based analyzers, or any other clinical diagnostic analyzer known in the art. Preferably, analyzer 110a is configured to test quality control materials having known properties to allow users to determine the accuracy of the analyzer and to provide assurance to users that the analyzer is operating within allowable tolerances. Clinical diagnostic analyzer 110a may be configured for use with various quality control materials, whether in liquid or lyophilized form, and may be configured for use in the immunoassay, serum chemistry, immunology, hematology, and other fields.

Looking to FIGS. 1 through 3 in combination, in typical use in performing a test on a patient specimen, the analyzer 110a prompts an user to load a patient specimen as depicted in FIG. 3C, and to perform an analysis as depicted in FIG. 3B once the sample is loaded. Upon completion of the test, the analyzer may prompt the user to store or review the data. Similarly, the analyzer may guide a user to load QC material as depicted in FIG. 3A.

It should be understood that the operation of the analyzer 100a may be performed locally, at the analyzer, or that the operation may be coordinated thorough the server 112 when the analyzer is operated in a system 100 as depicted in FIG. 1 It should be further understood that any data may be stored locally on the analyzer 110a, on the server 112 or database 114, and that the data may be made available throughout the system 100 and over the network 115 so that remote servers and analyzers may likewise access the stored data. Similarly, analyses may be run on the analyzer itself, on the server, or may be distributed among multiple analyzers and/or servers.

It should also be understood that data collected and/or stored on any of the individual clinical diagnostic analyzers in any of the systems may be shared and communicated to other clinical diagnostic analyzers in that same system or laboratory, may be shared and communicated with the server and database within that system, and may be shared and communicated to other systems, and to the clinical diagnostic analyzers and servers and databases within those other systems.

Looking to FIG. 4, in one exemplary embodiment, a plurality of clinical diagnostics systems 150a, 150b, 150c, 150n, each of which are similar to that depicted in FIG. 1, are in communication via a network 152, such as the Internet or other WAN. This collection of separate systems comprises a peer group 154 of systems, wherein each system 150a, 150b, 150c, 150n represents a laboratory having one or more clinical diagnostic analyzers, and wherein each of laboratories conducts testing of patient specimens and quality control materials. Most preferably, each member 150a, 150b, 150c, 150n of the peer group 154 is a laboratory at a location geographically dispersed from the other peer group member laboratories, with each laboratory having similar types of clinical diagnostic analyzers, running similar types of tests and using quality control materials similar to those used by other members of the peer group.

In embodiments of the invention described herein, the analyses performed on multiple analyzers and the data collected by members of the peer group may be analyzed in combination to provide an output or result based on data collected across multiple analyzers, and based on data collected by other members of the peer group.

While known methods of performing crossover studies rely on manual collection and analysis of data over a period of ten to twenty days, the system and method of the present invention performs a virtual crossover study using either a single clinical diagnostic analyzer, multiple diagnostic analyzers, or single or multiple clinical diagnostic systems as members of a peer group to perform a virtual crossover study to allow a laboratory to immediately begin using a new lot of quality control material by using estimated mean and standard deviation values based on data obtained from a peer group already using the new lot of QC material.

With the configuration of clinical diagnostic analyzers, systems employing clinical diagnostic analyzers, and peer groups of clinical diagnostic analyzers set forth, systems and methods for conducting virtual crossover studies in accordance with the present invention will now be described.

As discussed above, conducting a crossover study generally involves determining the statistical behavior of a new lot of quality control material, namely, the mean and standard deviation of the new material. Because clinical diagnostic analyzers are used to analyze test specimens and patient specimens, until a laboratory can ascertain the parameters of the new lot of quality control material, it cannot be certain of the accuracy of the results of analyses performed on actual specimens.

In accordance with an exemplary embodiment of the present invention, a virtual crossover study allows a peer group of clinical diagnostic analyzers to share data to allow calculation of an estimated mean and standard deviation (SD) for a new lot of quality control material before any analyses have been run on the new lot of material at a laboratory wishing to crossover to the new material. Then, as analyses are completed on the new lot of QC material, that actual test data is incorporated into the estimation of the mean and SD. Once a sufficient number of analyses are completed—typically ten data points—the calculation of the mean and SD continues with data only from the actual analyses. Thus, the system and method of the present invention allow the crossover study to begin using virtual data—i.e., data obtained from the peer group—to predict or estimate a mean and a SD for a new lot of QC material, before any new analyses are run and to augment those estimated values with actual data as analyses on the new lot of quality control material are completed.

The mean and standard deviation (SD) of a new lot of QC material can be predicted by using data collected from the peer group relating to the old lot of quality control material, using the following equations:

$$D = L\bar{x}_{old} / G\bar{x}_{old}$$

$$L\hat{x}_{new} = D * G\bar{x}_{new}$$

$$\widehat{Lsd}_{new} = (L\hat{x}_{new} * CV_{old})/100$$

Where:

D is the bias of the laboratory with respect to the peer group based on a prior or old lot of quality control material;

$L\bar{x}_{old}$ is the laboratory mean from the prior lot of quality control material;

$G\bar{x}_{old}$ is the peer group mean from the prior lot of quality control material;

$G\bar{x}_{new}$ is the peer group mean from the new lot of quality control material;

$L\hat{x}_{new}$ is the initial prediction for the laboratory mean of the new lot of quality control material;

$CV_{old}$ is the coefficient of variation from the prior lot of quality control material; and $\widehat{Lsd}_{new}$ is the initial prediction for the laboratory standard deviation (SD) of the new lot of quality control material.

Note that the coefficient of variation CV is sometimes referred to as a relative standard deviation (RSD) and can be expressed as the ratio of the standard deviation to the mean.

Using the above equations in a manner as will be described below, a predicted mean ($L\hat{x}_{new}$) and predicted SD ($\widehat{Lsd}_{new}$) for a new lot of quality control material is calculated using data from the peer group, adjusted by a calculated bias D between the laboratory and the peer group.

These predicted values are used initially, then augmented with data values obtained from actual analyses run by the laboratory on the new lot of quality control materials, as will be explained in more detail below, wherein the predicted values are phased out as the new actual values are obtained in weighted calculations, as follows:

Updated $L\hat{x}_{new} = W_1 * L\hat{x}_{new} + W_2 * L\bar{x}_{new}$; where $W_1 = (N_T - N_Q)/N_T$ $W_2 = N_Q/N_T$ Updated $\widehat{Lsd}_{new} = $(Updated $L\hat{x}_{new} * CV_{old})/100$;

Wherein:

$L\bar{x}_{new}$ is the mean of the data collected for the new lot of quality control material ($N_Q$ data points);

$W_1$ is the weight applied to the predicted mean of the new lot of quality control material;

$W_2$ is the weight applied to the mean computed on a new lot of data;

$N_T$ is the number of planned samples for the crossover study, preferably $N_T$ will be at least ten (10);

$N_Q$ is the number of samples collected so far from the new lot of quality control material, i.e., a count of completed new analyses on the new lot;

Updated $L\hat{x}_{new}$ is the updated prediction for the mean of the new lot of quality control material; and Updated $\widehat{Lsd}_{new}$ is the updated prediction for the SD of the new lot of quality control material.

When the target number of samples, $N_T$ have been collected, the virtual crossover study is complete and the estimates for the mean and SD of the new lot will rely only on newly collected data.

Figure 5:
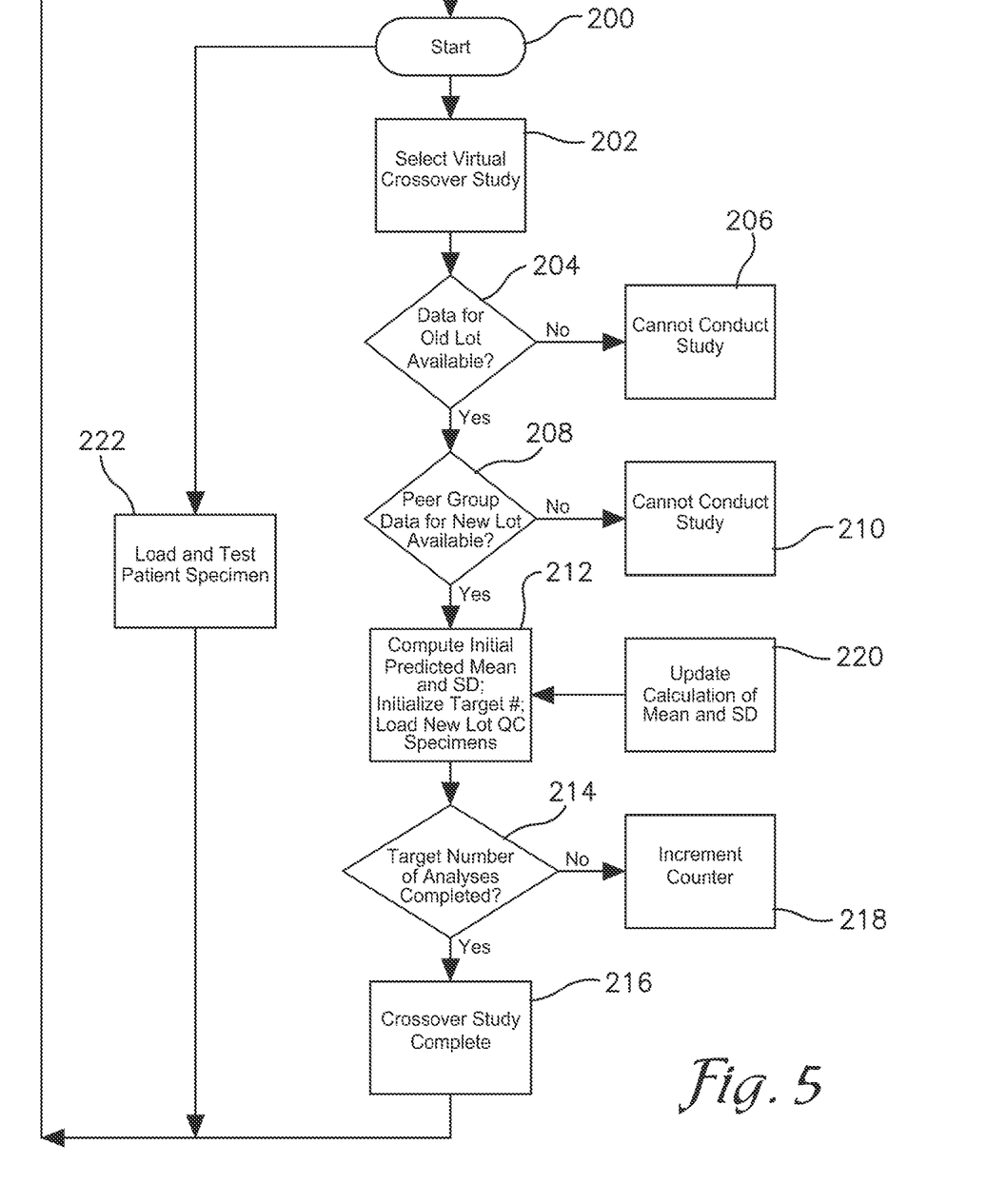
FIG. 5 is a flow diagram of an exemplary method for conducting a virtual crossover study in accordance with an exemplary embodiment of the present invention.

With the initial parameters and equations for conducting a virtual crossover study generally set forth, the steps for implementing a virtual crossover study in accordance with an exemplary embodiment of the present invention are depicted in the flow diagram of FIG. 5.

Looking first to FIG. 5, a method for conducting a virtual crossover study using a clinical diagnostic analyzer begins at block 200. As can be seen in the figure, the process of loading and testing patient specimens using the clinical diagnostic analyzer at block 222 may occur in parallel with, i.e., concurrently with, an ongoing virtual crossover study as will now be described.

At block 202, in response to a prompt presented by a clinical diagnostic analyzer, such as depicted in FIG. 3D, a user selects a new lot of control material to use, and, as depicted in FIG. 3B, selects to conduct a virtual crossover study on the selected new lot of quality control material.

At block 204, the analyzer determines whether data associated with the old, prior lot of control material which had been in use on the analyzer is available on the analyzer, from another analyzer in the laboratory, from the server or database, or from any other source, memory, or storage accessible by the analyzer. If no data can be located with respect to the old lot of control material, at block 206 the virtual crossover study cannot be conducted, and the process ends.

At block 208, the analyzer determines whether peer group data associated with the new lot of control material is available on the analyzer, from another analyzer in the laboratory, from the server or database, from a member of the peer group, or from any other source, memory, or storage accessible by the analyzer. If no peer group data can be located with respect to the new lot control material, at block 210 the virtual crossover study cannot be conducted, and the process ends.

With data from the old lot of control material and from the peer group data with respect to the new lot of control material, at block 212, the analyzer begins the virtual crossover study by initially computing a predicted mean and standard deviation for the new lot of material as follows:

First, the bias of the laboratory conducting the study with respect to the peer group is accounted for by comparing the laboratory mean for the prior lot of QC material ($L\bar{x}_{old}$) to the peer group mean for the prior lot of QC material ($\overline{Gx}_{old}$). The bias (D) is calculated as: $D=(\overline{Lx}_{old}-\overline{Gx}_{old})/\overline{Gx}_{old}$.

With the bias (D) calculated, an initial prediction of the mean for the new lot of control material ($L\hat{x}_{new}$) is calculated by adjusting the peer group mean ($\overline{Gx}_{new}$) to account for the bias (D) as:

$$L\hat{x}_{new}=D*\overline{Gx}_{new},$$

and a predicted standard deviation for the new lot of control material ($\widehat{Lsd}_{new}$) is calculated based on that calculated predicted mean for the new lot of control material ($L\hat{x}_{new}$) and the coefficient of variation of the old lot of control material ($CV_{old}$) as:

$$\widehat{Lsd}_{new}=(L\hat{x}_{new}*CV_{old})/100$$

Still at block 212, with the predicted mean ($L\hat{x}_{new}$) and predicted standard deviation ($\widehat{Lsd}_{new}$) for the new lot of control material calculated, those values are used as initial values for the mean and standard deviation, and the virtual crossover study continues for a target number of analyses ($N_T$). $N_T$, the target number of analyses, or study size, is preferably initially set to ten so that ten analyses of the new lot of control material are conducted in the crossover study. In alternative embodiments, $N_T$ may be greater than ten. In a preferred embodiment, the target number of analyses ($N_T$) is preset at ten in the clinical diagnostic analyzer. In alternative embodiments, the operator may be prompted by the analyzer to enter a desired target number ($N_T$). In further embodiments, the target number ($N_T$) is obtained by the clinical diagnostic analyzer from the server, the database, or other source. It should be understood that the predicted mean and SD (($L\hat{x}_{new}$) and ($\widehat{Lsd}_{new}$) may be used by the clinical diagnostic analyzer in the testing of patient specimens at block 222 while the crossover study is still ongoing.

Finally, at block 212, a counter ($N_Q$) to count the number of analyses run in the analysis is initially set to zero. As analyses are conducted on the new lot of control material, as will be described below, the counter $N_Q$ is incremented as each subsequent analyses is run.

Moving to block 214, if the number of analyses run ($N_Q$) is greater than or equal to the target number of analyses to be run ($N_T$), then, at block 216 the virtual crossover study is complete.

If, at block 214, the number of analyses run ($N_Q$) is not greater than or equal to the target number of analyses to be run ($N_T$) then at block 218 the number of analyses run ($N_Q$) is incremented by one, and at block 220, the predicted mean $L\hat{x}_{new}$ and standard deviation $\widehat{Lsd}_{new}$ for the new lot of control material are updated using the just-acquired data from the analyses, as follows:

First, two weighting factors, $W_1$ and $W_2$, are calculated for use in allocating the weight or consideration to be given in subsequent calculations to the prior predicted mean ($L\hat{x}_{new}$) versus the mean derived from the data acquired from the actual analyses ($\overline{Lx}_{new}$), based on how many new analyses have been conducted ($N_Q$) compared to the target number of analyses ($N_T$). Those weighting factors are calculated as:

$$W_1=(N_T-N_Q)/N_T$$

$$W_2=N_Q/N_T$$

An updated predicted mean (updated $L\hat{x}_{new}$) and standard deviation (updated $\widehat{Lsd}_{new}$) for the new lot of control material are then calculated by incorporating the data acquired from the new analyses and using the weighting factors, as:

$$\text{updated } L\hat{x}_{new}=W_1*L\hat{x}_{new}+W_2*\overline{Lx}_{new}; \text{ and}$$

$$\text{updated } \widehat{Lsd}_{new}=(\text{Updated } L\hat{x}_{new}*CV_{old}/100.$$

With the updated predicted mean and updated standard deviation calculated, the process proceeds back to block 214, where, if the number of analyses run ($N_Q$) is greater than or equal to the target number of analyses to be run ($N_T$), then, at block 216 the virtual crossover study is complete, and, if not, then at block 218 the number of analyses run ($N_Q$) is incremented by one, and at block 220, the updated predicted mean $L\hat{x}_{new}$ and updated standard deviation $\widehat{Lsd}_{new}$ for the new lot of control material are calculated and updated using the just-acquired data from the $N_Q$ analysis in the manner as just described.

Thus, the calculation of the predicted mean and standard deviation continues for the target number of analyses ($N_T$), with the calculated values being updated with successive run, with the most recently acquired data point being incorporated into the calculation in a weighted fashion as previously described.

At block 214, when the target number of analyses have been completed, i.e, $N_Q$ is greater than or equal to $N_T$, then the process proceeds to block 216 where the crossover study is complete. Upon completion of the virtual crossover study, a user may begin or rejoin an ongoing testing of patient specimens at block 222 where a patient specimen is tested, with an operator prompted to load patient specimens into the analyzer, or the analyzer commanding an automated loading mechanism to load the specimens. It should be understood that the testing of patient specimens at block 222 may be conducted using the estimated mean and SD as calculated in block 212 while the crossover study is ongoing, prior to completion of the crossover study.

The method above thus provides a virtual crossover study that provides for calculating a predicted mean and standard deviation for a new lot of quality control material before conducting any analyses on the new lot by using data from a peer group laboratory with respect to that new lot of material. With the initial predicted values calculated, new data from analyses conducted on the new lot of material is incorporated into the calculations of the mean and standard deviation on a weighted basis. Once a target number of analyses are completed, any subsequent calculations of the mean and standard deviation of the QC control material are thus performed using only data from actual analyses.

As can be seen, the systems and methods of the present invention provide an improvement over the generally accepted twenty-day crossover study, and allow use of a predicted mean and standard deviation until a sufficient number of data points on a new lot of QC material can be collected.

While the present invention has been described and illustrated hereinabove with reference to various exemplary embodiments, it should be understood that various modifications could be made to these embodiments without departing from the scope of the invention. Therefore, the invention is not to be limited to the exemplary embodiments described and illustrated hereinabove, except insofar as such limitations are included in the following claims.

What is claimed and desired to be secured by Letters Patent is as follows:

1. A clinical diagnostic analyzer for conducting virtual crossover studies, comprising:
   a processor;
   measurement hardware in communication with the processor and configured to measure properties of an analyte;
   a memory device having stored thereon executable instructions that, when executed by the processor, cause the clinical diagnostic analyzer to perform operations comprising:
   acquiring data for an old lot of quality control material;
   acquiring data for a new lot of quality control material from a peer group of clinical diagnostic analyzers;
   calculating a predicted mean and standard deviation for the new lot of quality control material based on the acquired data for the old lot of quality control material and the acquired peer group data for the new lot of quality control material;
   storing in the memory device the calculated mean and standard deviation for use in in testing;
   running a target number of analyses on a specimen from the new lot of quality control material;
   updating the calculated predicted mean and standard deviation for the new lot of quality control material based on data acquired by the analyses, wherein updating the calculated predicted mean and standard deviation comprises weighting the effect of the data acquired by the analyses in the calculation based on the number of analyses completed;
   controlling and commanding an automated loading mechanism to load a patient specimen for testing; and
   testing the patient specimen using the updated mean and standard deviation.

2. The clinical diagnostic analyzer of claim 1, wherein calculating a predicted mean and standard deviation for the new lot of control material comprises:
   obtaining peer group data for a mean of the old lot of quality control material and a mean of the old lot of quality control material from the laboratory in which the clinical diagnostic analyzer is located; and
   calculating a bias based on the peer group data mean and the laboratory mean.

3. The clinical diagnostic analyzer of claim 2, wherein the memory device includes instructions, that when executed, further cause the clinical diagnostic analyzer to perform operations comprising:
   running an analysis on a specimen from the new lot of quality control material; and
   updating the calculated predicted mean and standard deviation for the new lot of quality control material based on data acquired by the analysis.

4. The clinical diagnostic analyzer of claim 1, wherein the memory device includes instructions, that when executed, further cause the clinical diagnostic analyzer to perform operations comprising:
   presenting a prompt on the input panel and display to a user to load a specimen into the measurement hardware; and
   accept an input from the user indicating that the specimen has been loaded.

5. The clinical diagnostic analyzer of claim 1, wherein the memory device includes instructions, that when executed, further cause the clinical diagnostic analyzer to perform operations comprising:
   alerting a user if the data for an old lot of quality control material or the data for a new lot of quality control material cannot be acquired.

6. The clinical diagnostic analyzer of claim 1, further comprising an input panel and display operable to present information and data from the processor to a user and to accept input and selections from a user.

7. A system for conducting virtual crossover studies, comprising:
   a plurality of peer group systems, wherein each peer group system comprises:
   a server comprising a processor, a memory and a database, wherein the server is in communication with servers of other peer group systems; and
   a plurality of clinical diagnostic analyzers in communication with the server, wherein each of the plurality of clinical diagnostic analyzers comprises:
   a processor;
   measurement hardware in communication with the processor and configured to measure properties of an analyte;
   a memory device having stored thereon executable instructions;
   wherein the executable instructions stored on the memory device of at least one of the clinical diagnostic analyzer, when executed by the corresponding processor, cause the clinical diagnostic analyzer to perform operations comprising:
   acquiring data for an old lot of quality control material;
   acquiring data for a new lot of quality control material from a peer group of clinical diagnostic analyzers;
   calculating a predicted mean and standard deviation for the new lot of quality control material based on the acquired data for the old lot of quality control material and the acquired peer group data for the new lot of quality control material;
   storing in the memory device the calculated mean and standard deviation for use in testing;
   running a target number of analyses on a specimen from the new lot of quality control material;
   updating the calculated predicted mean and standard deviation for the new lot of quality control material based on data acquired by the analyses, wherein updating the calculated predicted mean and standard deviation comprises weighting the effect of the data acquired by the analyses in the calculation based on the number of analyses completed;
   controlling and commanding an automated loading mechanism to load a patient specimen for testing; and
   testing the patient specimen using the updated mean and standard deviation.

8. The system of claim 7, wherein calculating a predicted mean and standard deviation for the new lot of control material comprises:
   obtaining peer group data for a mean of the old lot of quality control material and a mean of the old lot of quality control material from the laboratory in which the clinical diagnostic analyzer is located; and
   calculating a bias based on the peer group data mean and the laboratory mean.

9. The system of claim 8, wherein the memory device includes instructions, that when executed, further cause the clinical diagnostic analyzer to perform operations comprising:

running an analysis on a specimen from the new lot of quality control material; and updating the calculated predicted mean and standard deviation for the new lot of quality control material based on data acquired by the analysis.

10. The system of claim 7, wherein the memory device includes instructions, that when executed, further cause the clinical diagnostic analyzer to perform operations comprising:

presenting a prompt on the input panel and display to a user to load a specimen into the measurement hardware; and accept an input from the user indicating that the specimen has been loaded.

11. The system of claim 7, wherein the memory device includes instructions, that when executed, further cause the clinical diagnostic analyzer to perform operations comprising:

alerting a user if the data for an old lot of quality control material or the data for a new lot of quality control material cannot be acquired.

12. The system of claim 7, further comprising an input panel and display operable to present information and data from the processor to a user and to accept input and selections from a user.

13. The system of claim 7 wherein the memory device includes instructions, that when executed, further cause the clinical diagnostic analyzer to perform operations comprising:

verifying operation of the clinical diagnostic analyzer using the stored mean and standard deviation.

14. A method for conducting virtual crossover studies, comprising:

acquiring data for an old lot of quality control material;

acquiring data for a new lot of quality control material from a peer group;

calculating a predicted mean and standard deviation for the new lot of quality control material based on the acquired data for the old lot of quality control material and the acquired peer group data for the new lot of quality control material;

storing the calculated mean and standard deviation for use in testing;

verifying operation of a clinical diagnostic analyzer using the stored mean and standard deviation;

running an analysis on a specimen from the new lot of quality control material using the clinical diagnostic analyzer;

updating the calculated predicted mean and standard deviation for the new lot of quality control material based on data acquired by the analysis; wherein the data acquired by the analysis is weighted in the calculated predicted mean and standard deviation based on the number of analyses completed;

controlling and commanding, by the clinical diagnostic analyzer, an automated loading mechanism to load a patient specimen for testing and;

testing the patient specimen on the clinical diagnostic analyzer, wherein the clinical diagnostic analyzer uses the updated mean and standard deviation in the testing.

15. The method of claim 14, further comprising:

calculating a bias based on a peer group data mean and a laboratory mean; and using the calculated bias in calculating the predicted mean and standard deviation.

\* \* \* \* \*